United States Patent

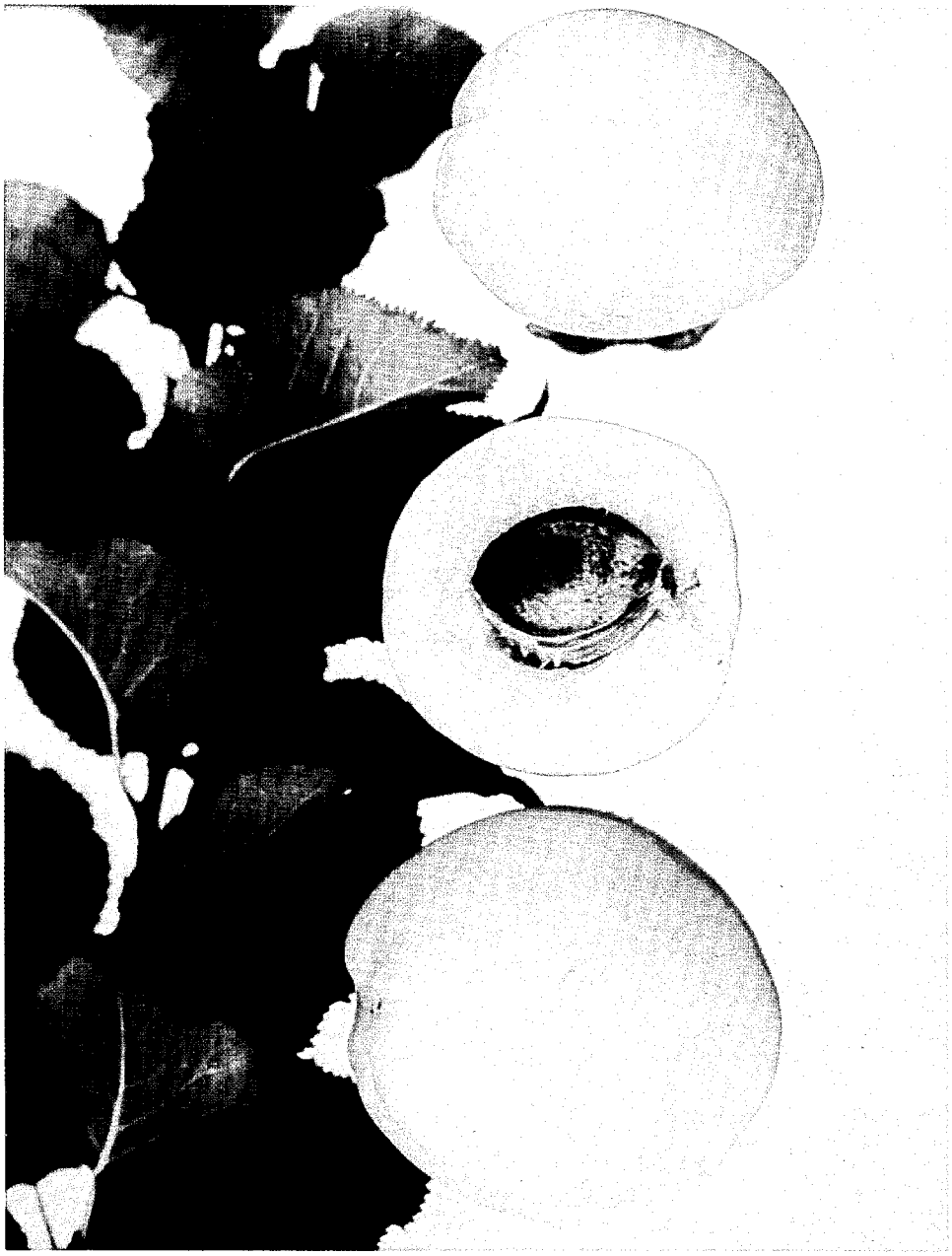

Plant Pat. 3,927
Patented June 29, 1976

3,927
APRICOT TREE

Raymond C. Freimann, Tieton, Wash., assignor to Stark Brothers Nurseries & Orchards Company, Louisiana, Mo.

Filed Feb. 26, 1975, Ser. No. 553,211
Int. Cl.[2] A01H *5/08*
U.S. Cl. Plt.—39 1 Claim

ABSTRACT OF THE DISCLOSURE

An apricot tree originated as a bud mutation of Tilton apricot.

SUMMARY OF THE INVENTION

This invention relates to apricot trees, of the Tilton type.

It was originated as a bud mutation of the Tilton apricot, in Tieton, Wash.

It is similar in type to the Tilton apricot, except that the fruit is larger.

It has been asexually reproduced by budding.

DETAILED DESCRIPTION OF DRAWING

The accompanying drawing shows typical specimens of the foliage and fruit (in side view and in section) of the new variety as depicted in color as nearly true as is reasonably possible to make the same in a color illustration of this character.

DETAILED DESCRIPTION OF DISCLOSURE

The following is a detailed description of my new variety with color terminology in accordance with Ridgway's Color Standards and Nomenclature, as indicated, except where general color terms of ordinary dictionary signifiance are obvious.

The specimens described were grown in Tieton, Wash. The first and last picking were from August 7 to August 12.

Tree: Large; vigorous; spreading; vase formed; hardy; productive; regular bearer.
Trunk: Stocky; shaggy.
Branches (2 years): Medium slender; green—Warbler Green Plate IV Color No. 23 Tone k—Ridgway.
Lenticels: Numerous; large.
Leaves: Length 2⅛"; width 2"; medium small; ovate; acutely pointed; medium thick; dark green—Rice Plate XVII Color No. 29′ Tone k—Ridgway.
Margin: Glandular; finely serrate.
Petiole: Medium long.
Glands: Average number—4 to 7; opposite; medium small; globose.
Flowers: Dates first and full blossoms, Mar. 10–20 in Pike County, Mo.; medium early; salmon.
Fruit: Over-ripe—August 8.
Size: Fairly uniform; large; axial diameter 2¾"; transverse in sture plans 2¾"; at right angles to suture plans 1¾".
Form: Uniform; symmetrical; transversely toward suture.
Suture: Deep; extends from base but discontinues at apex.

Ventral surface: Rounded; strongly lipped toward base at both sides.
*Cavity.*—Abrupt; elongated in suture plant with suture showing on one side; depth 3/16"; breadth ½"; markings, none.
*Base.*—Cuneate; rounded.
*Apex.*—Rounded; apical.
*Stem.*—Length ¼"; medium stout; pubescent; adherence to stone—strong.
Skin: Thick; medium tough; astringent; free.
*Color.*—Orange—Buff Plate III Color No. 15 Tone d—Ridgway; slightly blushed red—Light Salmon Orange Plate II Color No. 11 Tone d—Ridgway; scant; short; does not roll up when rubbed.
Flesh:
*Color.*—Yellow-orange—Buff Plate III Color No. 15 Tone d—Ridgway.
*Surface of pit cavity.*—Yellow.
*Amygadelin.*—Abundant; juice abundant; rich.
*Texture.*—Meaty.
*Fibres.*—Few; fine; tender.
*Ripens.*—Fairly even.
*Flavor.*—Mild; vinous.
*Aroma.*—Pronounced.
*Eating quality.*—Good.
Stone: Free.
*Fibres.*—Free; retains short fibre-like threads along ridges.
*Size.*—Large; length 1¼ inches; thickness ⅝ inch.
*Form.*—Oval.
*Base.*—Straight; narrow; oval.
*Apex.*—Rounded.
*Sides.*—Equal on right and left sides.
*Surface.*—Irregularly furrowed near ventral edge.
*Ridges.*—Rounded.
*Dorsal edge.*—Full; ridges on either side continuous.
Use: Market; dessert; canning.
Keeping quality: Medium poor.
Shipping quality: Good.
General notes: Identical to Tilton except that fruit is larger having an axial diameter of 2¾ inches, a transverse diameter in suture plane of 2¾ inches, and having a transverse diameter at right angles to suture plane of 1¾ inches, as compared with the Tilton apricot grown under similar environmental conditions having an axial diameter of 1¾ inches, a transverse diameter in suture plane of 1⅞ inches, and a transverse diameter at right angles to suture plane of 1½ inches.

The bud mutation of the Tilton apricot is essentially identical to the Tilton apricot except that the fruit is much larger and the halves are somewhat more compressed.

I claim:

1. A new and distinct variety of apricot tree, substantially as herein shown and described, characterized particularly as to novelty by being appreciably larger in size than the Tilton apricot.

No references cited.

ROBERT E. BAGWILL, Primary Examiner
J. R. FEYRER, Assistant Examiner